United States Patent [19]
Hakky

[11] Patent Number: 6,152,919
[45] Date of Patent: Nov. 28, 2000

[54] LASER RESECTOSCOPE

[75] Inventor: Said I. Hakky, Largo, Fla.

[73] Assignee: Canox International, Ltd., Largo, Fla.

[21] Appl. No.: 09/272,037

[22] Filed: Mar. 18, 1999

[51] Int. Cl.$^7$ .................................................. A61B 18/18
[52] U.S. Cl. ................................ 606/15; 606/14; 606/16; 606/41
[58] Field of Search .................... 606/13–16, 39, 606/40, 41, 49, 45, 170, 180, 167; 607/88, 89, 90–94, 100, 101

[56] References Cited

U.S. PATENT DOCUMENTS

| | | | |
|---|---|---|---|
| 5,312,399 | 5/1994 | Hakky et al. ............................... | 606/15 |
| 5,409,483 | 4/1995 | Campell et al. ........................... | 606/15 |
| 5,437,660 | 8/1995 | Johnson et al. ........................... | 606/15 |
| 5,487,740 | 1/1996 | Sulek et al. ............................... | 606/15 |
| 5,498,258 | 3/1996 | Hakky et al. ............................... | 606/15 |
| 5,549,601 | 8/1996 | McIntyre et al. .......................... | 606/15 |
| 6,007,570 | 12/1999 | Sharkey et al. ........................... | 607/96 |

*Primary Examiner*—John P. Leubecker
*Assistant Examiner*—Ahmed Farah
*Attorney, Agent, or Firm*—Rosenberg, Klein & Lee

[57] ABSTRACT

A resectoscope for laser coagulation and cutting of prostatic or bladder tissue. The resectoscope also uses a mechanical cutting element having sharp blades rotating at high speed to further cut the coagulated lased tissue. The combination of coagulating/cutting using the laser energy with further cutting by mechanical means allows the surgeon to perform this procedure more quickly and efficiently, and permits retrieval of the resected tissue for pathological examination.

3 Claims, 2 Drawing Sheets

LASER RESECTOSCOPE

BACKGROUND OF THE INVENTION

1. Field of the Invention

The present invention relates generally to a surgical device, and, in particular, to a laser resectoscope for coagulating, cutting and removing prostatic and bladder tissue in a patient.

2. Description of the Prior Art

There are many methods for treating the obstructing prostate in male patients. These methods are medical and surgical. Since the beginning of this century the surgical approach was the only means of treating the prostate growth. The surgical approach was open prostate surgery, by cutting the skin and muscle to remove the obstructing prostate manually. The other approach was the use of a resectoscope. The resectoscope is an elongated sheath which is passed urethrally to the obstructing prostate. Electricity is then passed through a wire which is directed to remove the obstructing prostate in small chips. These small chips are initially thrown into the urinary bladder. At the end of the procedure, the prostatic chips are evacuated from the bladder and sent for pathological examination. It is estimated that at least 6% of these so called benign prostatic growths will be diagnosed as cancer of the prostate. Such cancer will eventually kill the patient if left untreated.

At the beginning of the 1980s, laser energy was used to burn the prostate using a procedure called ablation or vaporization of the prostate. In ablation prostate surgery, the entire prostate is burned beyond recognition, i.e. charred. Such a procedure has many disadvantages. Dead charred tissue is left behind to slough over many months, causing great discomfort to the patient. In addition, such dead tissue may cause of tissue scarring or infection. Both complications are difficult to treat. In addition, at least 6% of the prostate cancer is missed. No tissue diagnosis was possible using laser ablation procedure.

One alternative to laser ablation surgery is a procedure in which the prostate tissue is coagulated using laser energy. The laser used for this procedure is a Neodymium:Yttrium-Aluminum-Garnet (Nd:YAG) laser. The laser fiber is used in contact (or non contact) with the bladder or prostatic tissue to coagulate and cut the targeted tissue. Many companies manufacture Nd:YAG lasers. One company is LaserSonics located in Milpitas, California. In the past few years a YAG:Holmium laser was introduced. Coherent Medical Group of Palo Alto, Calif. manufactures the YAG:Holmium laser. The Holmium laser has an advantage of lesser tissue penetration than the Nd:YAG laser. Thus, more precise coagulation and cutting of the prostatic and bladder tissue is possible.

Many articles have been written using the Holmium:YAG laser. Using lasers to coagulate the prostatic or bladder tissue has a major advantage in that tissue architecture is preserved for pathological diagnosis. Unfortunately, no tissue diagnosis was attempted for many years. In 1988, the first description of coagulating the prostate and then removal was described in the literature. The advantage of such procedure was the removal of the dead coagulated prostatic tissue. Thus, less pain during voiding and less incidence of urinary tract infection is experienced by the patient. Retrieving the coagulated prostatic or bladder tissue will make it possible to diagnose prostate cancer in 6% or more of patients. Prostatic cancer in these patients was shown to advance and eventually kill the patient.

Laser energy falls within a small portion of the electromagnetic spectrum, and its wavelength is calculated in metric units. The wavelength of the Holmium laser is 2100 nanometers, while the Nd:YAG laser has a wavelength of 1064 nanometers; both of these lasers operate within the near infrared electromagnetic spectrum.

Lasers can cut, coagulate and ablate tissue, depending on the wavelength, power and frequency of the device. The optical fiber transmitting the laser energy can be used to remove or coagulate the tissue in either a contact or non-contact mode. In the contact mode, the optical fiber transmitting the laser energy is in physical contact with the tissue, while in the non-contact mode, the fiber is positioned between a few millimeters to a few centimeters away from the tissue. In this node, the laser energy travels through the liquid irrigating medium, such as saline solution, before contacting the tissue.

Thus, laser energy can be used to coagulate and cut tissue, in addition to the mechanical cutting means, which facilitates and accelerates the removal of the excised tissue. The tissue can then be submitted to a laboratory for pathological examination.

In addition, the removal of the dead coagulated prostatic or bladder tissue will result in early removal of the Foley urethral catheter which is inserted immediately after the use of the laser. The Foley catheter will divert the urine from the lased prostate or bladder tissue. The Foley catheter causes irritation and infection to the patient. The Foley catheter can be removed within hours of the laser surgery, unlike the use of diathermy electrical current in the conventional resectoscope, when the Foley catheter is left indwelling between 2–4 days.

SUMMARY OF THE INVENTION

It is therefore the object of the present invention to coagulate and cut prostatic or bladder tissue using laser energy.

It is a further object of the present invention to use laser energy of different wavelengths to coagulate and cut prostatic or bladder tissue.

It is a further object of the present invention to provide a resectoscope which can operate in a rotating motion powered by a motor, thus increasing the speed and efficiency of endoscopic surgery of the bladder and prostate.

It is still a further object of the present invention to use mechanical cutting means to further cut the coagulated prostatic or bladder tissue.

It is still a further object of the present invention to use irrigation fluid to flush the coagulated and resected prostatic or bladder tissue to help improve of the operating field.

It is yet a further object of the present invention to use suction to assist in retrieval of the coagulated prostatic and bladder tissue for pathological examination.

These and other objects and advantages of the present invention will be more readily apparent in the description which follows.

DETAILED DESCRIPTION OF THE PREFERRED EMBODIMENT

Figure 1:
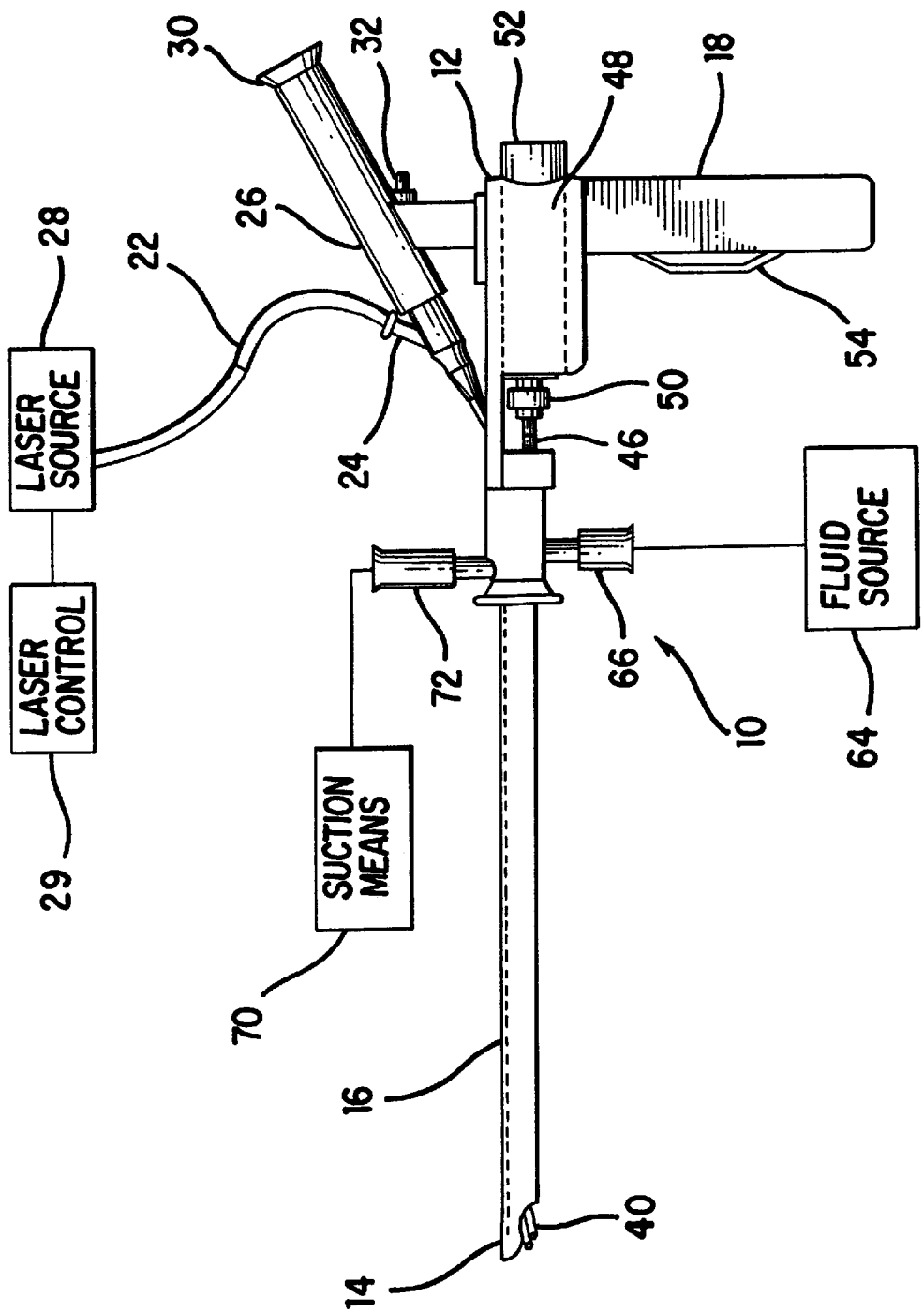
FIG. 1 is a side elevational view of the instrument of the present invention.
Figure 2:
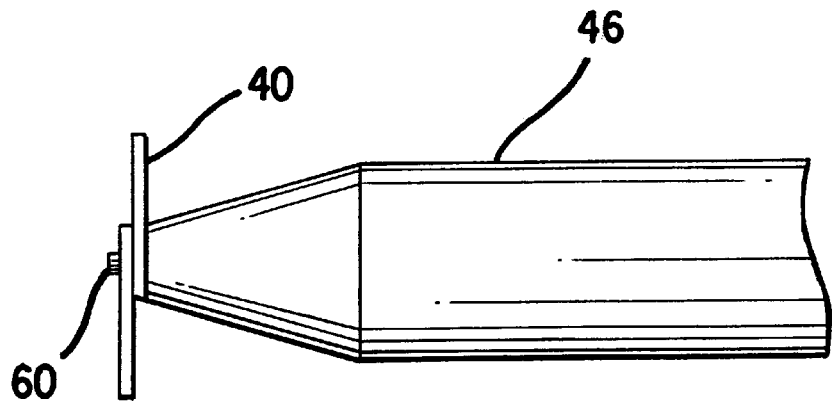
FIG. 2 is an enlarged side view of the mechanical cutting means of the instrument of the present invention.

Referring more particularly to the drawings, there is shown in FIG. 1a resectoscope device, generally indicated at 10, which embodies the principles of the present invention. Resectocope 10, which has a proximal end 12 and a distal end 14, contains an elongated hollow cylindical sheath member 16 extending from distal end 14 toward proximal end 12 where it is affixed to a handle 18. An inner sheath 20 is located within sheath member 16, extending from distal end 14 to handle 18. A fiber optic laser member 22 is located within inner sheath 20, extending from distal end 14 through a section of handle 18 and exiting from a port 24 of an optical imaging device 26. Laser member 22, which in the present embodiment has a diameter of between 400 and 1,000 microns, is connected to a source of laser energy 28, preferably operating in the near infrared electromagnetic spectrum, such as a Holmium:YAG laser, which is operated by a control means 29. Imaging device 26 terminates at proximal end 12 of the device 10 at an eyepiece 30, and also contains a lower port 32. Port 32 is adapted to be coupled to a light source (not shown) which will illuminate the surgical site at distal end 14 via an optical fiber 34, allowing the surgeon to visualize the operative field by looking through eyepiece 30.

A rotating cutting element 40 is positioned at distal end 14 of resectoscope 10, extending below a cutaway section 42 of sheath member 16. Cutting element 40, which in the present embodiment is a propeller-shaped blade have a pair of sharp edges 44, is affixed to a driving rod 46 which extends through sheath element 16 proximally toward handle 18 where it is coupled for rotation to an air motor 48 (located within handle 18) by a coupling joint 50. In the present embodiment, motor 48 is preferably powered by a rechargeable battery 52 located within handle 18. Motor 48 is actuated by a grip activated switch 54, which preferably controls the rotational speed of motor 48 proportionally to the force applied to switch 54.

Figure 3:
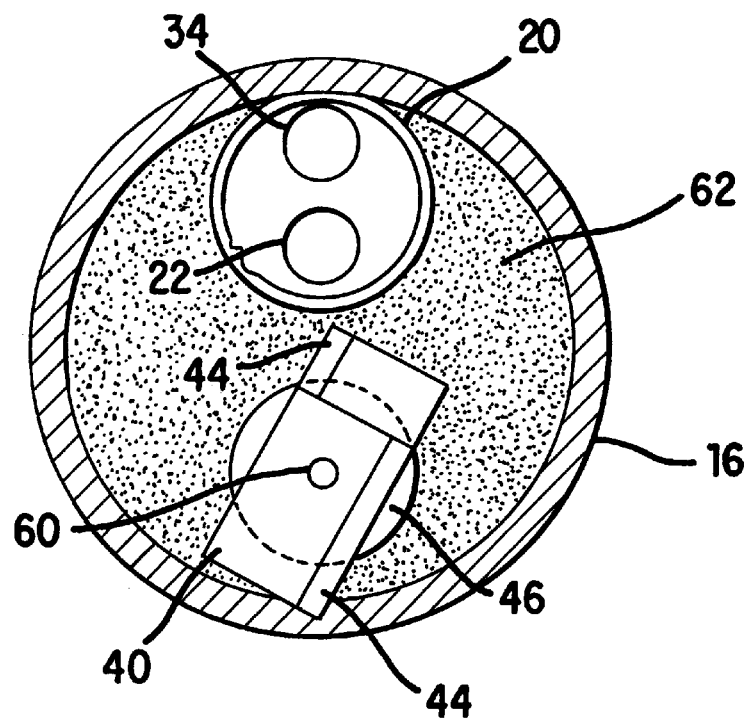
FIG. 3 is an end view of the instrument of the present invention showing the various cutting/coagulating parts in detail.

It should be noted that mechanical cutting element 40 is preferably releasably affixed to driving rod 46 by conventional means such as a screw 60 (FIG. 3) such that it can be removed and disposed of after each procedure. Also, this allows for cutting elements of different configurations to be used with resectoscope 10 to permit the optimal shape of cutter to be used for a particular procedure.

The interior area 62 within sheath element 16 is adapted to receive irrigation fluid from a fluid source 64 which is connected to an inlet port 66 on handle 18. Irrigation fluid, which is preferably saline solution, enters interior 62 of sheath element 16 through port 66 and flows distally toward end 14 to the surgical site. This fluid, along with blood, resected tissue and other debris, is carried away from the surgical site through inner sheath 20 by a vacuum generated by a suction means 70 which is connected to an outlet port 72.

Having described the elements of the device of the present invention, the operation of the preferred embodiment of resectoscope 10 will now be described. After lubricating sheath element 16 liberally, distal end 14 is inserted through the urethra to the prostate area or bladder as appropriate. Irrigation fluid, preferably normal saline (0.9% Sodium Chloride water solution), from source 64 passes through port 66 and travels through sheath member 16 to the surgical site. When the surgeon, viewing the site through eyepiece 30, has positioned resectoscope 10 at the proper site, he energizes control means 29 (via a foot pedal in the present embodiment), causing laser energy via fiber 22 to coagulate and cut the prostatic or bladder tissue, either by contacting the tissue (contact lasing) or by positioning fiber 22 within 1 or 2 centimeters of the tissue (non-contact lasing).

Using fiber 22 to coagulate and cut tissue will often result in removing very large pieces of prostatic and bladder tissue, which pieces will not pass through the sheath to a collection device at suction means 70. The surgeon will then actuate mechanical cutting element 40 to cut these pieces into very small tissue fragments which can be removed by suction means 70. By gripping switch 54 of handle 18, motor 48 is activated, causing element 40 to rotate, chopping the coagulated tissue.

The surgeon continues to cut and coagulate tissue using laser fiber 22 and cutting element 40 until he has removed all of the targeted tissue. In the present embodiment, it is estimated that 10 grams of prostate tissue can be removed per minute, as compared to approximately one gram per minute using conventional electrocautery techniques. In addition, the resected prostatic or bladder tissue can be retrieved from suction means 70 for pathological examination.

At the end of the procedure, the surgeon withdraws resectoscope 10, and inserts a Foley catheter into the patient for a few hours. Under the current procedures of electrocautery, an indwelling Foley catheter must be left in place for 2–4 days, requiring a longer hospital stay and more recovery time.

The entire procedure using the device of the present invention is performed faster and more precise, thus requiring less anesthesia and less irrigation fluid. In addition, laser coagulation is considered superior to electrocautery in tissue healing.

While the present invention has been shown and described in terms of a preferred embodiment thereof, it will be understood that this invention is not limited to this particular embodiment and that many changes and modifications may be made without departing from the true spirit and scope of the invention as defined in the appended claims. In addition, as used herein and in the claims, the words as "distal", "proximal", "top", "bottom", "side", and the like are used in conjunction with the drawings for purposes of clarity, and it will be appreciated that they do not limit the device to a particular orientation.

What is claimed is:

1. A laser resectoscope, comprising:

a longitudinally extended cylindrical member having a through bore extending between opposing proximal and distal end portions of said cylindrical member;

a handle coupled to said proximal end portion of said cylindrical member;

an inlet port having one end coupled in fluid communication to said through bore and an opposing end coupled to a fluid source for dispensing an irrigating fluid to a surgical site adjacent said distal end portion of said cylindrical member;

a suction lumen extending through said through bore, said suction lumen having an inlet opening disposed adjacent said distal end portion of said cylindrical member and an outlet port coupled to a vacuum source for aspiration of the irrigation fluid and debris from the surgical site;

a fiber optic laser member extending through said suction lumen, said fiber optic laser member having a distal end adjacent said distal end portion of said cylindrical member;

a Holmium laser source optically coupled to a proximal end of said fiber optic laser member, said laser source having a wavelength approximating 2100 nanometers and a predetermined output power level established to cut and coagulate organic tissue at the surgical site with a laser beam output from said distal end of said fiber optic laser member;

a motor mounted in said handle;

a longitudinally extended shaft extending through said through bore of said cylindrical member and having a first end coupled to said motor for rotation thereby;

a cutting element coupled to a second end of said shaft and adapted for slicing the organic tissue cut from the surgical site by said laser beam into sufficiently small tissue fragments to be aspirated into said suction lumen.

2. The laser resectoscope as recited in claim 1 where said motor is an electric motor and said handle includes a cavity for receiving a battery therein, said battery being selectively coupled to said electric motor for rotatively driving said cutting element.

3. The laser resectoscope as recited in claim 2 further comprising a switch mounted in a grip portion of said handle for controlling rotational speed of said motor in proportion to a force applied to said switch.

* * * * *